United States Patent [19]

Kammlade, Jr.

[11] 4,232,686

[45] Nov. 11, 1980

[54] METHOD AND APPARATUS FOR INDICATING THE ONSET OF PARTURITION

[76] Inventor: William G. Kammlade, Jr., 703 Taylor Dr., Carbondale, Ill. 62901

[21] Appl. No.: 874,464

[22] Filed: Feb. 2, 1978

[51] Int. Cl.³ .............................................. A61B 5/10
[52] U.S. Cl. .................................... 128/775; 128/361; 340/573
[58] Field of Search ............ 128/2 S, 2 R, 361, 2.1 A, 128/775; 340/573

[56] References Cited

U.S. PATENT DOCUMENTS

| | | | |
|---|---|---|---|
| 3,212,496 | 10/1965 | Preston | 128/2.06 |
| 3,273,559 | 9/1966 | Evans | 128/2 S |
| 3,520,294 | 7/1970 | Fuzzell et al. | 128/2 S |
| 3,582,935 | 6/1971 | Verhaeghe | 340/279 |
| 3,608,541 | 9/1971 | Hall | 128/2 S |
| 3,618,059 | 11/1971 | Allen | 340/224 |
| 3,641,540 | 2/1972 | Cutler et al. | 340/224 |
| 3,670,320 | 6/1972 | Palmer | 340/279 |
| 4,055,839 | 10/1977 | Skeggs | 340/279 |
| 4,147,160 | 4/1979 | Aranow et al. | 128/2 S |

FOREIGN PATENT DOCUMENTS 2416829 10/1975 Fed. Rep. of Germany ............ 128/2 S

OTHER PUBLICATIONS

"Baby Buzzer"-Foaling Alarm, Locust Farms, Inc., Kirtland, Ohio (U.S. Ser. No. 698,948).

Primary Examiner—Kyle L. Howell
Attorney, Agent, or Firm—Senniger, Powers, Leavitt and Roedel

[57] ABSTRACT

Apparatus for indicating at a distance the onset of parturition in animals including a radio transmitter and a source of electrical power adapted to be secured to the pre-parturient animal and a rupturable assembly adapted to be mounted across the vaginal orifice of the pre-parturient animal. The rupturable assembly has a preferred rupture line along which the assembly ruptures when the vaginal orifice distends during the onset of parturition. A switch, for connecting the transmitter to the source of electrical power, is secured to the rupturable assembly on one side of the preferred rupture line. A magnet holds the switch open while the rupturable assembly is unruptured in order to prevent the closing of a circuit between the transmitter and the source of electrical power. The magnet is secured to the rupturable assembly adjacent the switch but on the opposite side of the preferred rupture line therefrom. The switch is closed except when in close proximity to the magnet. At the onset of parturition the rupturable assembly ruptures, separating the switch from the magnet. The switch thereupon closes, completing a circuit between the transmitter and the source of electrical power, causing the transmitter to transmit a radio signal indicative of the onset of parturition.

8 Claims, 4 Drawing Figures

METHOD AND APPARATUS FOR INDICATING THE ONSET OF PARTURITION

BACKGROUND OF THE INVENTION

This invention relates to monitoring apparatus and more particularly to a method and apparatus for indicating at a distance the onset of parturition in animals.

Present devices for monitoring parturition include closed circuit television systems, in which a person continuously watches a television screen for signs of parturition; radio monitoring systems, in which a person must continuously listen to a radio receiver for sounds of parturition; transmitting apparatus strapped around the girth of the pre-parturient animal, which is triggered by the female assuming a predetermined position during labor; an apparatus in which a pregnant sow is placed so that the first piglet born lands on a plate causing a bell to ring; an elastic belt fitted around the abdomen of a pregnant woman and connected to an X-Y recorder to record the pattern of uterine contractions during labor; and electrical apparatus connected to the lips of the cervix for providing a continuous indication at the site of the patient of the dilation of the cervix prior to the actual birth of an infant. Representative patents in which the latter two techniques are disclosed are U.S. Pat. Nos. 3,520,294 and 3,273,559.

A user of any of the above apparatus will obtain an accurate indication of the onset of parturition only if he continually monitors the apparatus or the animal assumes the predetermined position while giving birth. Using the closed circuit television system as an example, if the user happens to doze off while watching the monitor, the birth might occur while the observer is asleep. Additionally, most of the devices described above require that the pregnant animal be at a specific place. The closed circuit television system, for example, requires that the animal be within the field of view of the camera. The majority of the other systems require that the animal by physically in or attached to the rest of the apparatus during monitoring. Clearly these constraints are undesirable in the case of a large animal, such as a pregnant cow or mare, if she is to be monitored for any length of time.

SUMMARY OF THE INVENTION

Among the several objects of the present invention may be noted the provision of apparatus which indicates the onset of parturition without requiring continual visual monitoring; the provision of such apparatus which does not require continual auditory monitoring; the provision of such apparatus which is not dependent upon the animal being in a specific position; and the provision of such apparatus which does not require that the pregnant animal be at a specified location.

Briefly, apparatus of the present invention for indicating at a distance the onset of parturition in animals includes a radio transmitter and a source of electrical power adapted to be secured to the preparturient animal and a rupturable assembly adapted to be mounted across its vaginal orifice. The rupturable assembly has a preferred rupture line along which the assembly ruptures when the vaginal orifice distends during the onset of parturition. The apparatus of the present invention also includes a switch for connecting the transmitter to the source of electrical power, which switch is secured to the rupturable assembly on one side of the preferred rupture line. Adjacent the switch, but on the opposite side of the preferred rupture line, is means for preventing the switch from completing a circuit between the transmitter and the source of electrical power while the rupturable assembly is unruptured. The state of the switch except when it is proximate the preventing means is such as to complete the circuit between the transmitter and the source of electrical power. At the onset of parturition, the rupturable assembly ruptures, separating the switch from the preventing means. As a result, the circuit is completed between the transmitter and the source of electrical power, and the transmitter transmits a radio signal indicative of the onset of parturition.

The method of the present invention comprises securing the transmitter and source of electrical power to the pre-parturient animal and mounting the above-described rupturable assembly across its vaginal orifice. Other objects and features will be in part apparent and in part pointed out hereinafter.

BRIEF DESCRIPTION OF THE DRAWINGS

Corresponding reference characters indicate corresponding parts through the several views of the drawings.

DESCRIPTION OF A PREFERRED EMBODIMENT

Figure 4:
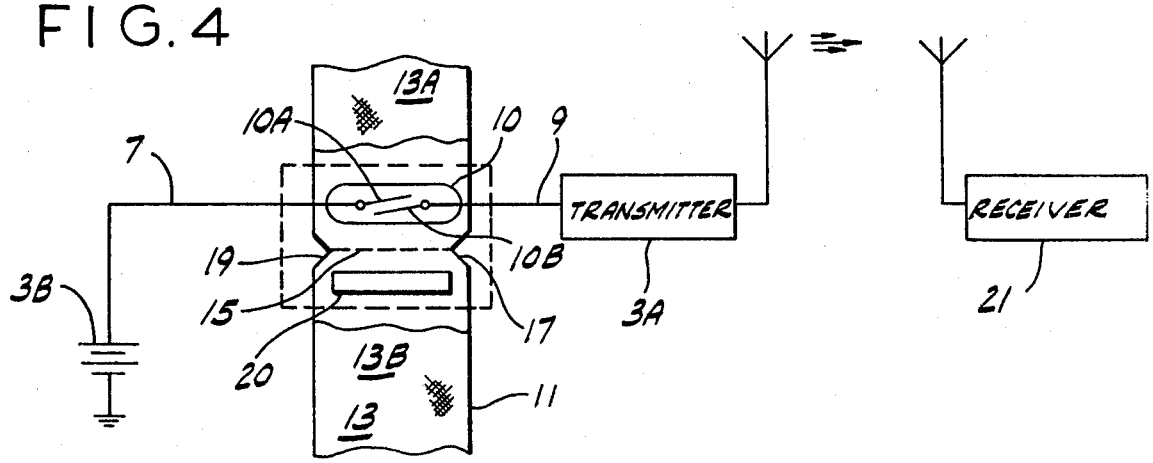
FIG. 4 is a schematic of the electrical circuit of the present invention.

Referring now to the drawings, apparatus of the present invention is shown generally at 1 and includes a housing 3 which is securable to the hindquarters, legs or tail of the pre-parturient animal, in this case a mare 5, by means of a glue such as that sold under the trade designation "Bull Cement" by the Minnesota Mining and Manufacturing Company of St. Paul, Minnesota. Housing 3 can also be secured to the animal by means of a patch or strip of the material sold under the trade designation "Velcro" by Velcro Inc. of Manchester, New Hampshire. Housing 3 is preferably relatively small, about the size of three half-dollars, and contains a ratio transmitter 3A (FIG. 4) having a preferred range of around 300 feet or more and a source of electrical power 3B, e.g., a battery. Transmitter-battery combinations such as are commonly sold as small pocket paging transmitters are suitable for use as transmitter 3A and battery 3B. Of course, any similar transmitter and battery would also work.

Although transmitter 3A and battery 3B are in the same housing 3, there is not a complete circuit between them inside the housing. The positive side of battery 3B, instead of being directly connected to transmitter 3A, is connected to a wire 7 which passes outside of housing 3. Likewise, transmitter 3B is connected to a wire 9 which passes outside of housing 3. The other ends of wires 7 and 9 are connected to a reed switch 10 which is secured to a rupturable assembly 11, best seen in FIG. 3, which is mountable across the vaginal orifice of preparturient mare 5. Rupturable assembly 11 includes a generally flat, elongate strip 13 having a preferred rupture line 15 intermediate the ends of the strip which divides the strip into two portions, designated by the reference characters 13A and 13B. Rupturable assembly 11 is made of tape such as that sold under the trade designation "Dermacel First-Air Tape" by Johnson & Johnson of New Brunswick, New Jersey. Plastic hospital tape could, of course, also be used. The length of rupturable assembly 11 can be varied but it is preferred that it be of such a length that portion 13A may be secured adjacent or directly to the labia, designated by the reference character 14A, on one side of the vaginal orifice and portion 13B may be secured adjacent or directly to the labia, designated by the reference character 14B, on the opposite side of the vaginal orifice. The ends of rupturable assembly 11 may be secured adjacent or directly to labia 14A and 14B of pre-parturient mare 5 by mechanical clips, but it is preferred that they be glued in place. The preferred glue is a strong, quick-setting glue such as that sold under the trande designation "Krazy Glue" by Krazy Glue, Inc. of Chicago, Illinois.

To ensure that rupturable assembly 11 ruptures along preferred rupture line 15, the assembly is perforated along line 15, thereby forming a line of weakness, and is notched at both ends of the line, the notches being indicated by the reference numerals 17 and 19. Of course, rupturable assembly 11 need not be both notched and perforated; depending upon the strength of the tape used in making rupturable assembly 11, notches alone or perforations alone may be sufficient to ensure that assembly 11 ruptures along preferred rupture line 15 when the vaginal orifice distends during the onset of parturition.

Reed switch 10 is secured to portion 13A of rupturable assembly 11 adjacent preferred rupture line 15. Reed switch 10 has two overlapping reeds, designated by the reference characters 10A and 10B. Reed 10A is connected to wire 7 and reed 10B is connected to wire 9, so that when reeds 10A and 10B contact each other switch 10 connects transmitter 3A to battery 3B. Together reed switch 10 and wires 7 and 9 constitute means for connecting the transmitter to battery 3B. Thus, when reed switch 10, which is disposed intermediate transmitter 3A and battery 3B, is closed, it completes a circuit between said transmitter and said battery, thereby causing power to be supplied to the transmitter.

A magnet 20, which constitutes means for preventing reed switch 10 from completing a circuit between transmitter 3A and battery 3B when rupturable assembly 11 is unruptured, is secured to rupturable assembly 11 adjacent switch 10 but on the opposite side of line 15. That is, magnet 20 is secured to portion 13B of assembly 11. The magnetic field from magnet 20 holds reeds 10A and 10B apart as long as rupturable assembly 11 is unruptured. On the other hand, when magnet 20 is not proximate switch 10, the magnetic field from magnet 20 in the vicinity of reed switch 10 decreases greatly and the state of switch 10 becomes such as to complete the circuit between transmitter 3A and battery 3B, i.e., reeds 10A and 10B naturally contact each other.

Figure 1:
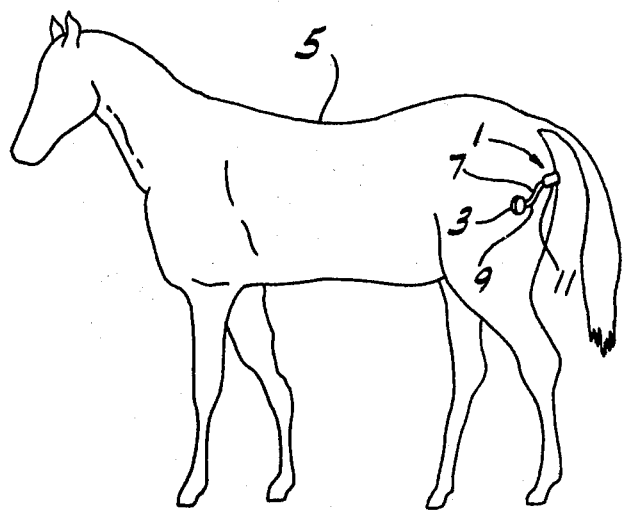
FIG. 1 is a perspective schematic of the apparatus of this invention mounted on a pre-parturient mare.
Figure 2:
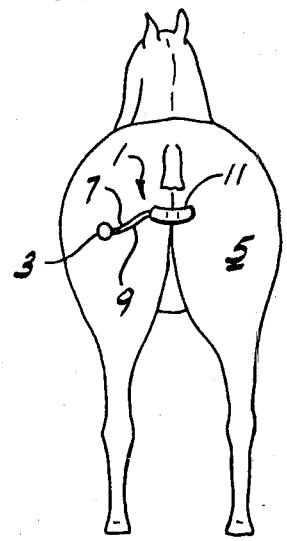
FIG. 2 is a right side view of FIG. 1 with the mare's tail removed.
Figure 3:
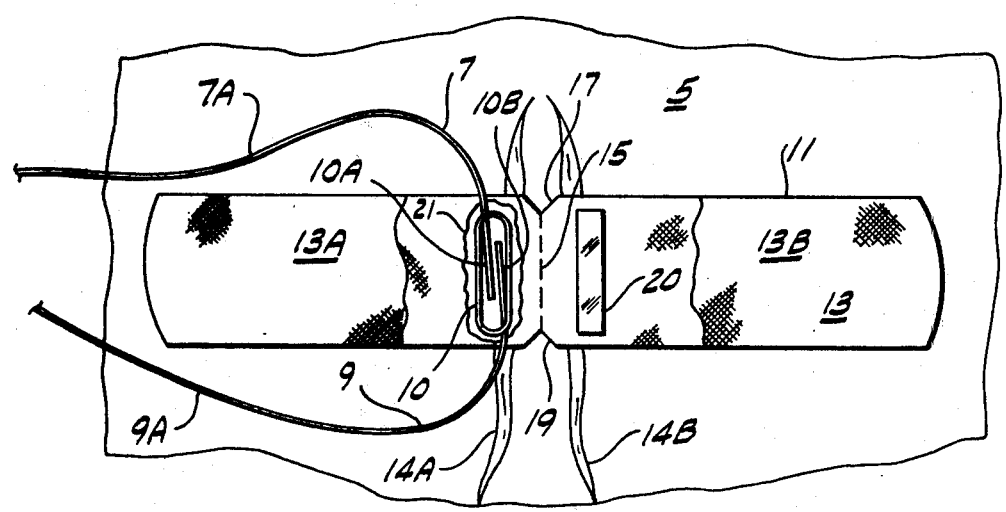
FIG. 3 is a perspective drawing, on an enlarged scale, of the rupturable assembly of the present invention mounted across the vaginal orifice of the preparturient animal with a portion of the assembly removed.

It should be noted that reed switch 10 should be potted in epoxy, designated by the reference numeral 21 (FIG. 3) or some other waterproofing agent, and that wires 7 and 9 should be covered with waterproof insulation, designated by the reference characters 7A and 9A (FIG. 3). That is, epoxy 21 and insulation 7A and 9A constitute means for protecting the circuit between the transmitter and the battery from water. This is because the location of rupturable assembly 11 on mare 5 makes it likely that fecal matter will be present, which could, in the absence of adequate waterproofing, prematurely complete the circuit between transmitter 3A and battery 3B.

It should also be noted that the location of rupturable assembly 11 is such that it is very difficult for mare 5 to rub assembly 11 off. Her tail effectively protects assembly 11 from such rubbing. Assembly 11 thus stays attached to the labia until the onset of parturition.

At the onset of parturition, the vaginal orifice distends, causing labia 14A and 14B to separate. (This occurs significantly only at the time of birth, particularly during the expulsion of the chorioallantoic membranes and the fetus.) This relative motion of labia 14A and 14B ruptures rupturable assembly 11 along preferred line 15, thereby separating reed switch 10 from magnet 20. As a result an electrical circuit between transmitter 3A and battery 3B is completed through reed switch 10. Thereupon, transmitter 3A transmits a radio signal indicative of the onset of parturition.

This parturition radio signal is received by a radio receiver 21 which indicates the reception of the parturition radio signal. Receiver 21 is left on constantly, even while the farmer sleeps. Receipt of the parturition radio signal causes receiver 21 to emit a loud beep or other audible tone to warn the farmer to attend mare 5.

Transmitter 3A and receiver 21 are both of common design such as may be found in a paging system. Since transmitter 3A is only on during parturition, the life of battery 3B is extended, and therefore transmitter 3A and battery 3B may be reused.

In view of the above, it will be seen that the several objects of the invention are achieved and other advantageous results attained.

As various changes could be made in the above methods and products without departing from the scope of the invention, it is intended that all matter contained in the above description or shown in the accompanying drawings shall be interpreted as illustrative and not in a limiting sense.

What is claimed is:
1. Apparatus for indicating at a distance the onset of parturition in animals comprising:
 a radio transmitter and a source of electrical power adapted to be secured to the pre-parturient animal at a position some distance from the vaginal orifice of said animal;
 a rupturable assembly adapted to be mounted across the vaginal orifice of the pre-parturient animal and having a preferred rupture line so that when the vaginal orifice distends during the onset of parturition the assembly ruptures along the preferred rupture line; connecting means for connecting the transmitter to the source of electrical power, said means including a switch disposed intermediate the transmitter and the source of electrical power which switch when closed completes a circuit therebetween, thereby causing power to be supplied to the transmitter, said switch being secured to the rupturable assembly on one side of the preferred rupture line;
 means for preventing the switch from completing a circuit between the transmitter and the source of electrical power while the rupturable assembly is unruptured, said preventing means being secured to the rupturable assembly adjacent the switch but on the opposite side of the preferred rupture line from the switch, the state of said switch except when it is proximate said preventing means being such as to complete the circuit between the transmitter and the source of electrical power, whereby at the onset of parturition the rupturable assembly ruptures, separating the switch from the preventing means, thereby completing a circuit between the transmitter and the source of electrical power, causing the transmitter to transmit a radio signal indicative of the onset of parturition.

2. Apparatus as set forth in claim 1 wherein the switch is a reed switch and the preventing means is a magnet.

3. Apparatus as set forth in claim 1 further including means for protecting the circuit from water.

4. Apparatus as set forth in claim 1 further including radio receiver means for indicating the reception of the parturition radio signal.

5. Apparatus as set forth in claim 1 wherein the rupturable assembly comprises a generally flat, elongate strip having the preferred rupture line intermediate the ends of the strip, thereby dividing the strip into two portions, said rupturable assembly having a length such that one portion may be secured on one side of the vaginal orifice and the other portion may be secured on the opposite side of the vaginal orifice, thereby mounting said assembly across said orifice.

6. Apparatus as set forth in claim 5 wherein the elongate strip is perforated along the preferred rupture line.

7. Apparatus as set forth in claim 5 wherein the elongate strip is notched at the ends of the preferred rupture line.

8. A method of indicating at a distance the onset of parturition in animals comprising:
securing a radio transmitter and a source of electrical power to a pre-parturient animal at a position some distance from the vaginal orifice of said animal;
mounting a rupturable assembly having a preferred rupture line across the vaginal orifice of the preparturient animal so that when the vaginal orifice distends during the onset of parturition the assembly ruptures along the preferred rupture line, said assembly having secured thereto a switch, which when closed completes a circuit between the transmitter and the source of electrical power, and means for preventing the switch from completing a circuit between the transmitter and the source of electrical energy while the rupturable assembly is unruptured, said switch being disposed on one side of the preferred rupture line and said preventing means being disposed adjacent said switch but on the opposite side of the preferred rupture line, the state of said switch except when it is proximate said preventing means being such as to complete the circuit between the transmitter and the source of electrical power, whereby at the onset of parturition the rupturable assembly ruptures, separating the switch from the preventing means, thereby completing a circuit between the transmitter and the source of electrical power, causing the transmitter to transmit a radio signal indicative of the onset of parturition; and
receiving the radio signal indicative of the onset of parturition on radio receiver means.

* * * * *